US009403145B2

(12) United States Patent
Dixit et al.

(10) Patent No.: US 9,403,145 B2
(45) Date of Patent: Aug. 2, 2016

(54) ORGANOMETALLIC COMPOUND PREPARATION

(71) Applicants: Dow Global Technologies LLC, Midland, MI (US); Rohm and Haas Electronic Materials LLC, Marlborough, MA (US)

(72) Inventors: Ravindra S. Dixit, Lake Jackson, TX (US); Hua Bai, Lake Jackson, TX (US); Curtis D. Modtland, Lake Jackson, TX (US); Robert A. Ware, Wellesley, MA (US); John G. Pendergast, Jr., Lake Jackson, TX (US); Christopher P. Christenson, Seguin, TX (US); Deodatta Vinayak Shenai-Khatkhate, Danvers, MA (US); Artashes Amamchyan, Bedford, MA (US); Kenneth M. Crouch, Shrewsbury, MA (US); Robert F. Polcari, Winchendon, MA (US)

(73) Assignees: Dow Global Technologies LLC, Midland, MI (US); Rohm and Haas Electronic Materials LLC, Marlborough, MA (US)

(*) Notice: Subject to any disclaimer, the term of this patent is extended or adjusted under 35 U.S.C. 154(b) by 39 days.

(21) Appl. No.: 14/642,704

(22) Filed: Mar. 9, 2015

(65) Prior Publication Data

US 2015/0174552 A1    Jun. 25, 2015

Related U.S. Application Data

(62) Division of application No. 13/586,751, filed on Aug. 15, 2012, now Pat. No. 9,006,475.

(60) Provisional application No. 61/523,582, filed on Aug. 15, 2011.

(51) Int. Cl.
*B01J 19/24* (2006.01)
*C07F 7/00* (2006.01)
(Continued)

(52) U.S. Cl.
CPC .............. *B01J 19/2405* (2013.01); *C07B 61/00* (2013.01); *C07F 5/00* (2013.01); *C07F 5/003* (2013.01); *C07F 7/006* (2013.01); *B01J 2219/00051* (2013.01); *B01J 2219/24* (2013.01)

(58) Field of Classification Search
CPC ............. C07F 5/00; C07F 5/003; C07F 7/006; B01J 19/2405; C07B 61/00
USPC .................................................. 422/129, 198
See application file for complete search history.

(56) References Cited

U.S. PATENT DOCUMENTS

| 3,016,396 A | 1/1962 | Irie et al. |
| 4,251,453 A | 2/1981 | Garrison |

(Continued)

FOREIGN PATENT DOCUMENTS

| CN | 1872861 A | 12/2006 |
| CN | 1872862 A | 12/2006 |

(Continued)

*Primary Examiner* — Porfirio Nazario Gonzalez
(74) *Attorney, Agent, or Firm* — S. Matthew Cairns

(57) ABSTRACT

An apparatus for continuously manufacturing organometallic compounds is provided where the apparatus has a source of a first reactant stream wherein the first reactant comprises a metal; a source of a second reactant stream; a laminar flow contacting zone for cocurrently contacting the first reactant stream and the second reactant stream; a mixing zone comprising a turbulence-promoting device; and a heat transfer zone.

7 Claims, 10 Drawing Sheets

(51) Int. Cl.
*C07F 5/00* (2006.01)
*C07B 61/00* (2006.01)

(56) References Cited

U.S. PATENT DOCUMENTS

| | | | |
|---|---|---|---|
| 4,925,962 A | 5/1990 | Beard et al. | |
| 4,948,906 A | 8/1990 | Beard | |
| 5,951,820 A | 9/1999 | Ohsaki et al. | |
| 6,495,707 B1 | 12/2002 | Leese et al. | |
| 7,112,691 B2 | 9/2006 | Tsudera et al. | |
| 7,166,734 B2 | 1/2007 | Shenai-Khatkhate et al. | |
| 7,179,931 B2 | 2/2007 | Tsudera et al. | |
| 8,101,787 B2 | 1/2012 | Lipiecki et al. | |
| 8,969,608 B2 * | 3/2015 | Modtland | B01J 14/00 422/198 |
| 2009/0023940 A1 | 1/2009 | Lipiecki et al. | |

FOREIGN PATENT DOCUMENTS

| | | | | |
|---|---|---|---|---|
| EP | 1303336 | | 9/2006 | |
| JP | 3215195 | | 7/2001 | |
| JP | 2010120935 A | | 6/2010 | |
| JP | 2013-67608 A | * | 4/2013 | ............ B01J 14/00 |
| WO | WO 9740053 | | 10/1997 | |
| WO | 2011094293 A1 | | 8/2011 | |

* cited by examiner

ORGANOMETALLIC COMPOUND PREPARATION

This application is a divisional application of U.S. Ser. No. 13/586,751, filed on Aug. 15, 2012, which claims the benefit of priority under 35 U.S.C. §119(e) to U.S. Provisional Application No. 61/523,582, filed Aug. 15, 2011, the entire contents of which application are incorporated herein by reference.

The present invention relates to the field of metal-containing compounds and particularly to the field of preparing organometallic compounds.

Metal-containing compounds are used in a variety of applications, such as catalysts and sources for growing metal films. One use of such compounds is in the manufacture of electronic devices such as semiconductors. Many semi-conducting materials are manufactured using well-established deposition technologies that employ ultrapure metalorganic (organometallic) compounds, for example, metalorganic vapor phase epitaxy, metalorganic molecular beam epitaxy, metalorganic chemical vapor deposition and atomic layer deposition.

Many of these organometallic compounds or their starting materials pose significant challenges in handling, due to their reactivity with air, pyrophoricity and/or toxicity. Care must be taken in the manufacture of these organometallic compounds. Conventional organometallic compound manufacturing methods are small-scale batch processes where it is relatively easy to control the reaction and exclude oxygen. The product yields from these batch processes vary across a wide range. For example, conventional batch-processes for manufacturing trimethylgallium, triethylgallium, and trimethylindium have yields of 80-100% before purification. Although these processes are effective, they allow only for limited production of the desired compounds. The need for larger amounts of these organometallic compounds means that many such small-scale production runs must be performed, which greatly increases the cost of the desired compounds.

U.S. Pat. No. 6,495,707 discloses a method of continuously manufacturing trimethylgallium ("TMG") by adding both gallium trichloride and trimethylaluminum to a reaction center in a distillation column, vaporizing the TMG produced and collecting the TMG from the top of the distillation column. The figure in this patent shows the reactants entering the column from opposing inlets. The apparatus in this patent appears to be designed to give turbulent flow for rapid mixing of the reactants. Turbulent flow is defined as having a Reynolds number ("Re") of ≥4000. However, the yields of TMG obtained from this process are low, only 50-68%, and the purity of the obtained TMG is not discussed.

Chinese published patent application CN 1872861 A discloses an improvement to the process of U.S. Pat. No. 6,495,707 in which a nitrogen gas stream is introduced into the bottom of the distillation column to increase agitation in the liquid phase portion in the column and to promote the generation of TMG, purporting to improve the reaction efficiency. However, the reported yields of TMG in this patent application are still low, only 52%, and are no different from those reported in U.S. Pat. No. 6,495,707.

There remains a need for a method of continuously preparing organometallic compounds in high yield.

The present invention provides a method of continuously preparing an organometallic compound comprising: (a) providing an apparatus comprising a reactor unit, the reactor unit comprising a laminar flow contacting zone, a mixing zone comprising a turbulence-promoting device, and a heat transfer zone; (b) continuously delivering a first reactant stream and a second reactant stream to the contacting zone to form a reaction mixture stream, wherein the first reactant stream and the second reactant stream are cocurrent and have substantially laminar flows, and wherein the first reactant is a metal-containing compound; (c) conveying the reaction mixture stream from the contacting zone to a heat transfer zone, and then to the mixing zone; (d) causing the reaction mixture stream to form an organometallic compound product stream; (e) controlling the temperature and pressure of the product stream in the heat transfer zone so as to maintain a majority of the organometallic compound in a liquid phase; and (f) conveying the product stream to a separation unit to isolate the organometallic compound.

Also provided by the present invention is an apparatus for continuously manufacturing an organometallic compound comprising: (a) a source of a first reactant stream wherein the first reactant comprises a metal; (b) a source of a second reactant stream; (c) a laminar flow contacting zone for cocurrently contacting the first reactant stream and the second reactant stream; (d) a mixing zone comprising a turbulence-promoting device; and (e) a heat transfer zone.

Figure 1:
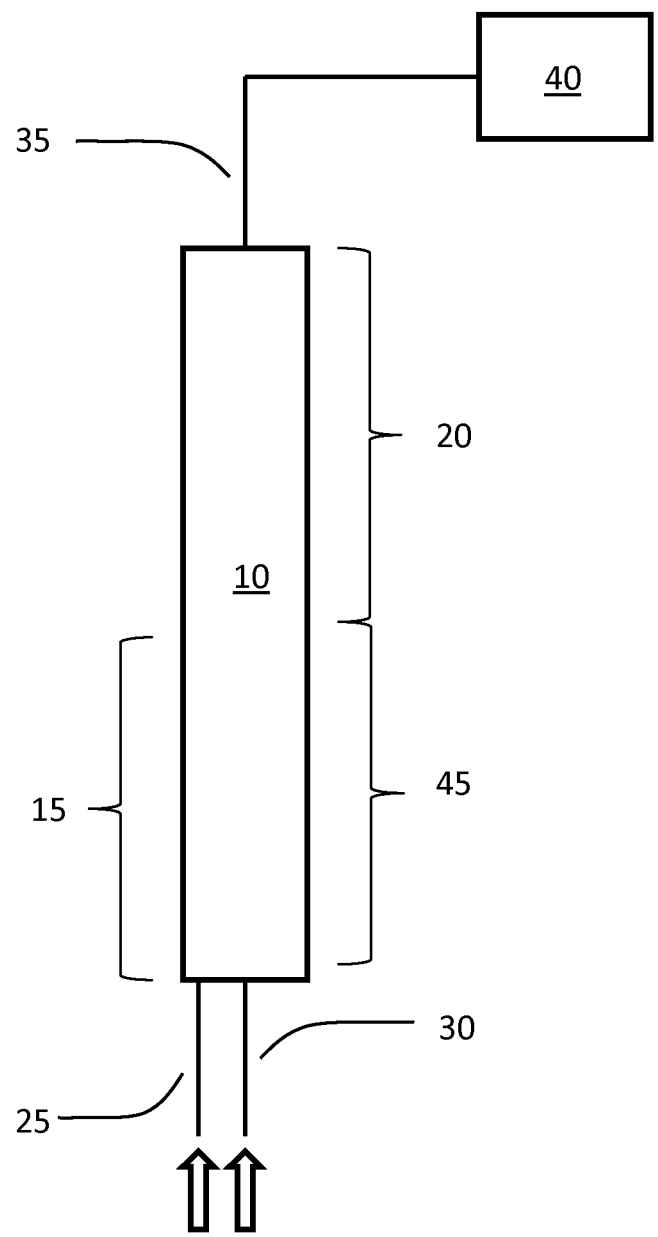
FIGS. 1-3 are schematic depictions of apparatuses of the invention suitable for use with the process of the invention.

The articles "a" and "an" refer to the singular and the plural. "Alkyl" includes straight chain, branched and cyclic alkyl. "Halogen" refers to fluorine, chlorine, bromine and iodine. The term "plurality" refers to two or more of an item. "Stream" refers to the flow of a fluid. "Fluid" refers to a gas, a liquid, or a combination thereof. The term "cocurrent" refers to the flow of two fluids in the same direction. The term "countercurrent" refers to the flow of two fluids in opposing directions. The following abbreviations shall have the following meanings: ppm=parts per million; m=meters; mm=millimeters; cm=centimeters; kg=kilograms; kPa=kilopascals; psi=pounds per square inch; and °C.=degrees Celsius. In the figures, like numerals refer to like elements.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms first, second, third, etc. may be used herein to describe various elements, components, regions, layers, zones or sections, these elements, components, regions, layers, zones or sections should not be limited by these terms. These terms are only used to distinguish one element, component, region, layer, zone or section from another element, component, region, layer, zone or section. Thus, a first element, component, region, layer, zone or section discussed below could be termed a second element, component, region, layer, zone or section without departing from the teachings of the present invention.

Furthermore, relative terms, such as "lower" or "bottom" and "upper" or "top," may be used herein to describe one element's relationship to another element as may be illustrated in the Figures. It will be understood that relative terms are intended to encompass different orientations of the device in addition to the orientation depicted in the Figures. For example, if the device in one of the Figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise noted, all amounts are percentages by weight and all ratios are molar ratios. All numerical ranges are inclusive and combinable in any order except where it is clear that such numerical ranges are constrained to add up to 100%.

The present invention provides a method for the continuous preparation of organometallic compounds. An apparatus comprising one or more reactor units may be used, where each reactor unit comprises: (a) a source of a first reactant stream wherein the first reactant comprises a metal; (b) a source of a second reactant stream; (c) a laminar flow contacting zone for cocurrently contacting the first reactant stream and the second reactant stream; (d) a mixing zone comprising a turbulence-promoting device; and (e) a heat transfer zone. Suitable reactors may include a plurality of mixing zones and/or a plurality of heat transfer zones. In this method, a first reactant stream is continuously delivered to the contacting zone of the reactor unit, and a second reactant stream is continuously delivered to the contacting zone to form a reaction mixture stream. The flows of the first reactant stream and the second reactant stream are cocurrent and substantially laminar. At least the first reactant is a metal-containing compound. The second reactant may optionally be a metal-containing compound, depending upon the particular reactants used and the organometallic compound desired. The reaction mixture stream is subjected to conditions to form an organometallic product stream and the temperature and pressure of the product stream are controlled in the heat transfer zone so as to maintain a majority of the organometallic compound in a liquid phase. The organometallic product stream is then conveyed from the reactor unit to a separation unit to isolate the organometallic compound.

A variety of different reactor units may be used in the present process. FIG. 1 is a schematic diagram of an apparatus suitable for use with the process of the invention having reactor 10 having a contacting zone 15, a mixing zone 20, and a heat transfer zone 45. Each of contacting zone 15, mixing zone 20, and heat transfer zone 45 may be any suitable length. In FIG. 1, contacting zone 15 and heat transfer zone 45 are shown to be co-extensive, but that is not required. Reactor 10 has a first inlet 25 and a second inlet 30 for feeding the first and second reactant streams, respectively, into contacting zone 15. Reactor 10 has an outlet 35 which is in fluid communication with separation unit 40.

Referring to FIG. 1, in operation, the first reactant stream 17 is conveyed into contacting zone 15 of reactor 10 by way of first inlet 25. The second reactant stream 27 is conveyed into contacting zone 15 of reactor 10 by way of second inlet 30. The flows of the first reactant stream and the second reactant stream in the contacting zone are cocurrent and laminar. The resultant reaction mixture stream is conveyed along reactor 10 and into mixing zone 20, which is designed to promote turbulence. The organometallic compound product stream exits reactor 10 by way of outlet 35 and is then conveyed to separation unit 40 where the desired organometallic compound is separated from by-products, unreacted first and second reactants, and the like.

Figure 2:
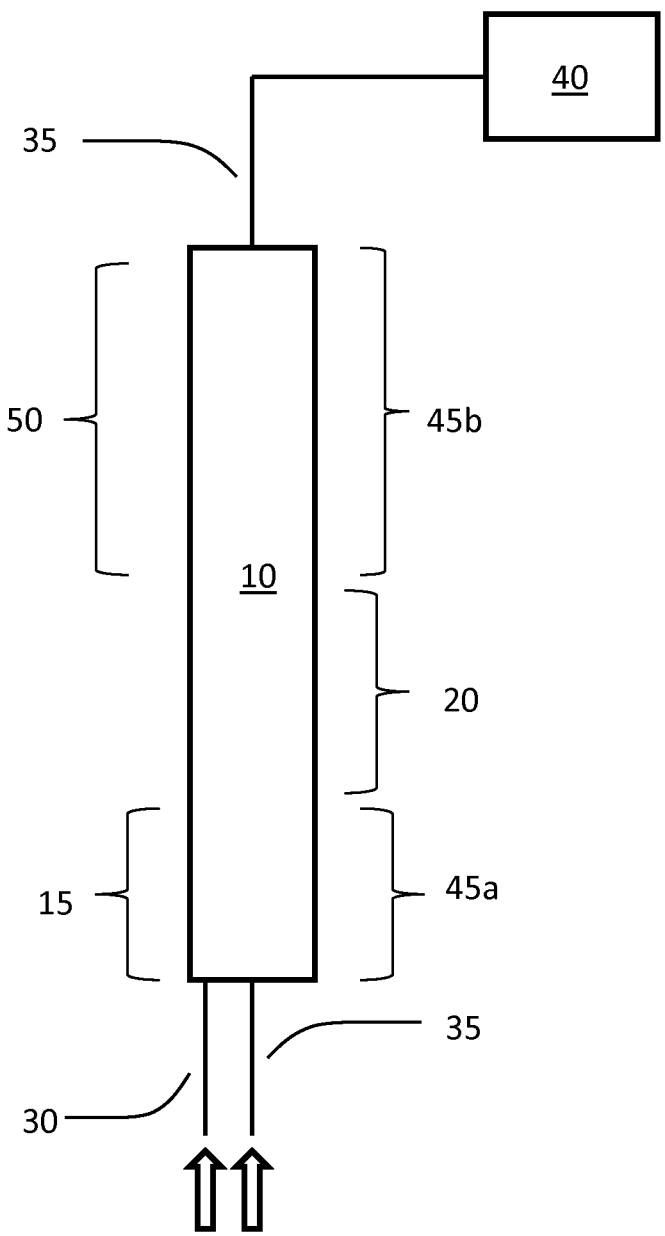

FIG. 2 shows an alternate reactor similar to that shown in FIG. 1, except that reactor 10 also includes a reaction zone 50 following mixing zone 20. Reactor 10 also has a plurality of heat transfer zones 45, with one heat transfer zone 45a being coextensive with contacting zone 15, and a second heat transfer zone 45b being co-extensive with reaction zone 50. It will be appreciated by those skilled in the art that mixing zone 20 may also be contained within a heat transfer zone, not shown, and that the heat transfer zones need not be co-extensive with either of the contacting zone or the reaction zone.

Figure 3:
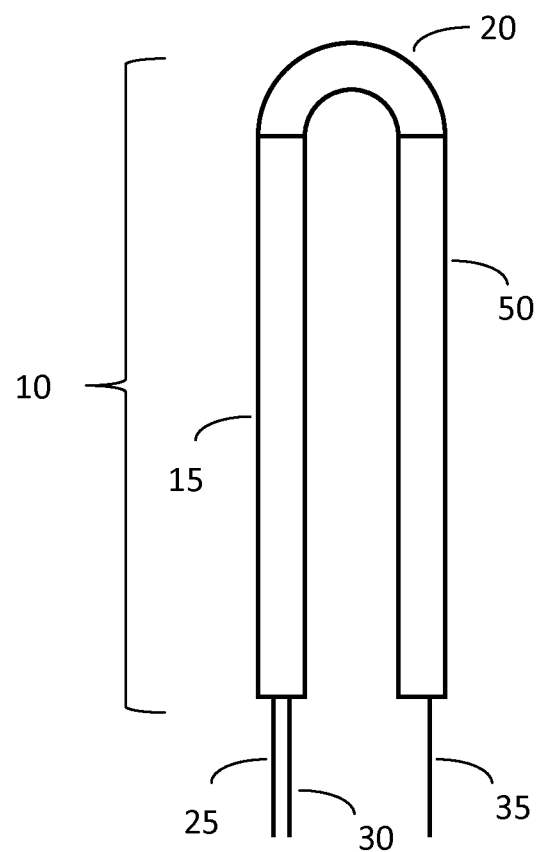

FIG. 3 illustrates a yet another suitable reactor 10 having contacting zone 15, mixing zone 20, and reaction zone 50. Each of the contacting zone, mixing zone and reaction zone may be contained within one or more heat transfer zones, not shown in FIG. 3. Mixing zone 20 is illustrated as a "U-bend" (180°), but other suitable bend configurations including 45°, 90°, and 360° bends, not shown, may be used.

Figure 4A:
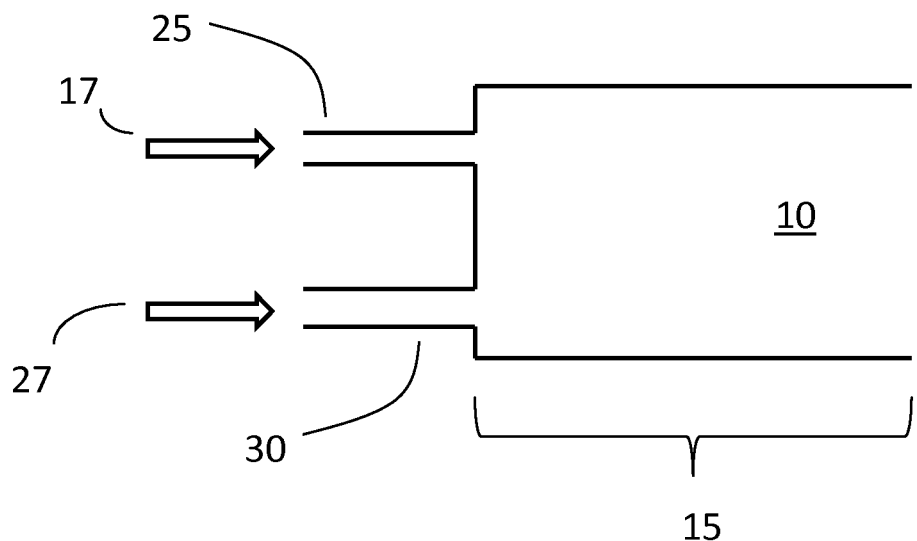
FIGS. 4A-4F are schematic cross-sectional depictions of suitable contacting zone inlets for use in an apparatus suitable for the process of the invention.
Figure 4B:
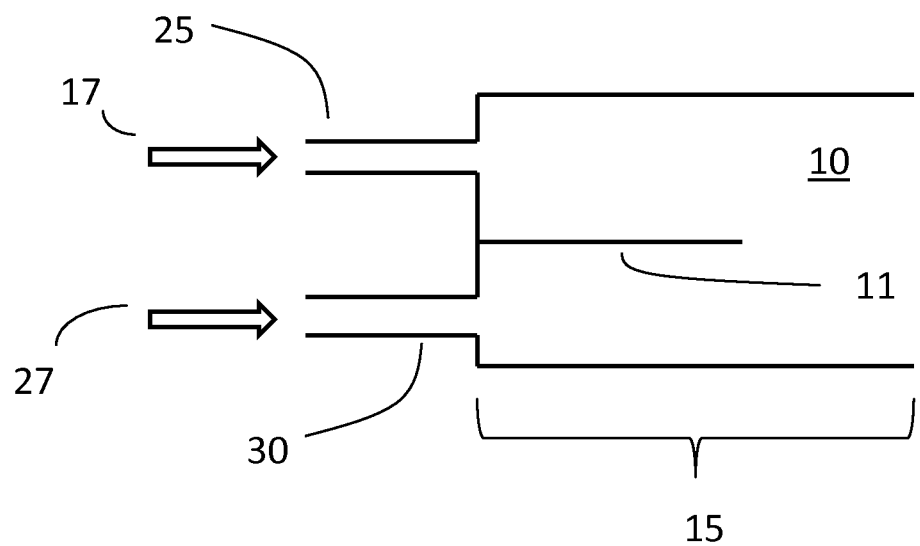
Figure 4C:
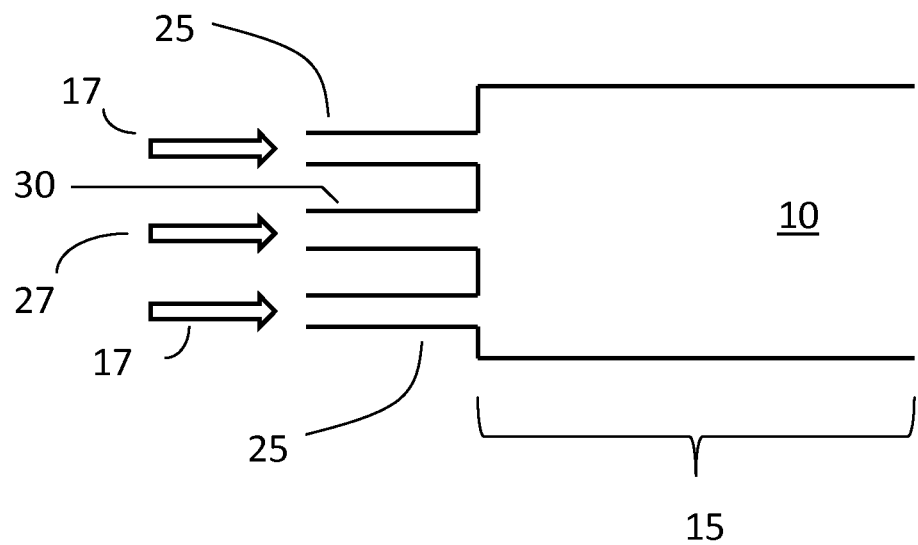
Figure 4D:
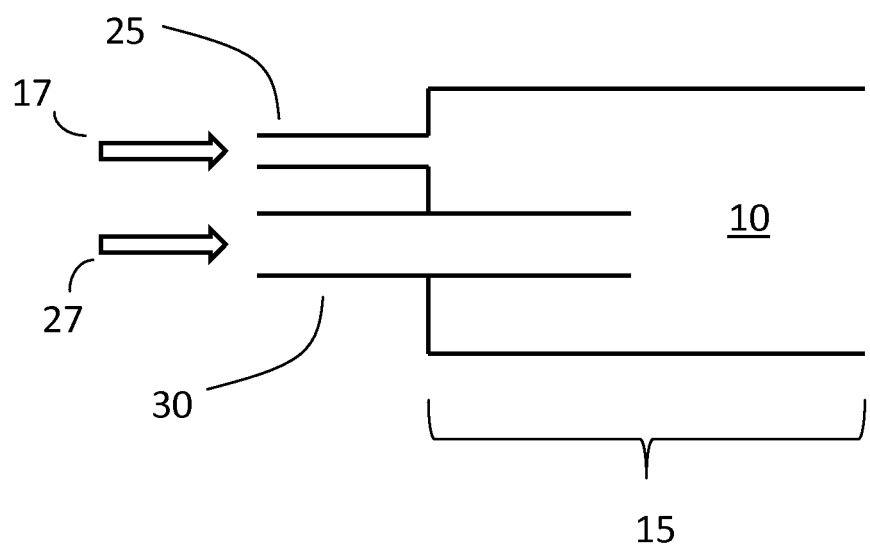
Figure 4E:
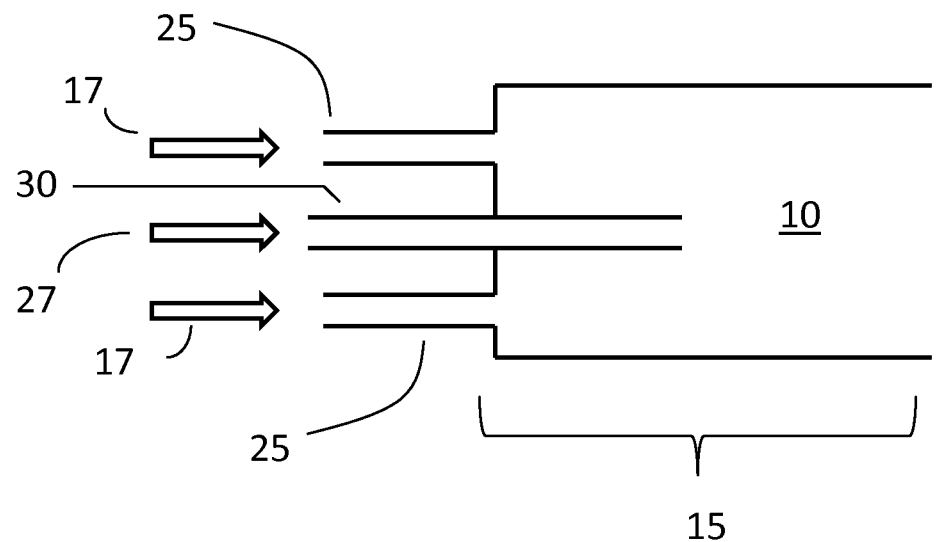
Figure 4F:
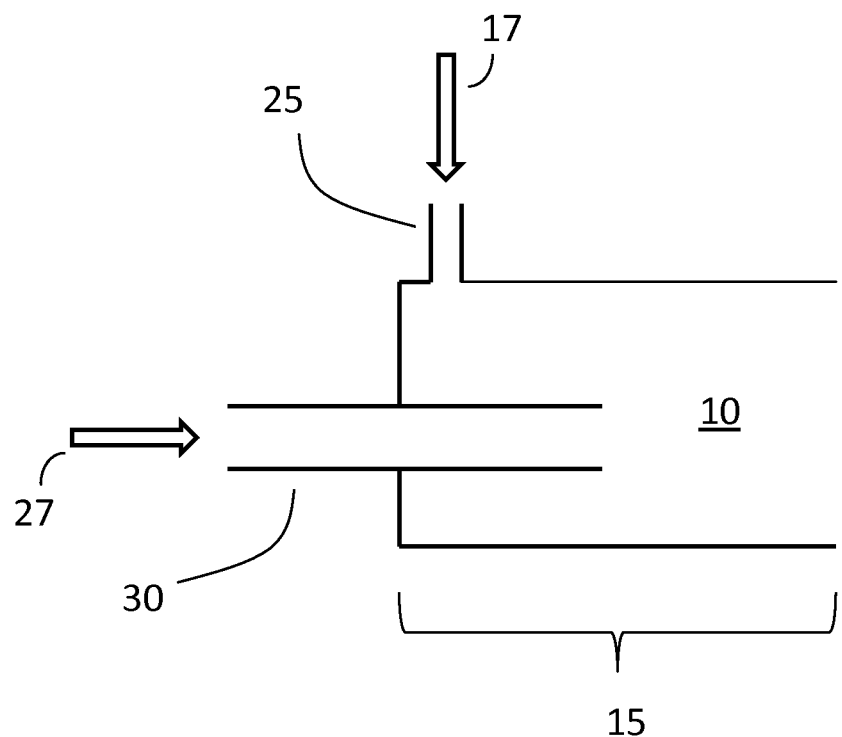

Referring to FIG. 1, first reactant stream 17 and second reactant stream 27 are delivered to contacting zone 15 with laminar flows. FIGS. 4A-4F are schematic cross-sectional views of alternate contacting zone 15 of reactor 10. FIG. 4A illustrates contacting zone 15 in rector 10 having a single first inlet 25 and a single second inlet 30, the second inlet being located in the relative center of the end of reactor 10. FIG. 4B illustrates contacting zone 15 similar to that in FIG. 4A, except that a baffle plate 11 is present to delay the onset of contact of first reactant stream 17 and second reactant stream 27. An alternate contacting zone 15 is shown in FIG. 4C having a plurality of first inlets 25 (only 2 are shown) and a single second inlet 30. FIG. 4D illustrates a further alternative of contacting zone 15 where second inlet 30 extends into reactor 10. In FIG. 4E, another alternative contacting zone 15 is illustrated having a plurality of first inlets 25 (only 2 are shown) and having second inlet 30 extending into reactor 10. FIG. 4F illustrates an alternate contacting section similar to that shown in FIG. 4D. The plurality of first inlets 25 in FIGS. 4C and 4E may be arranged in any pattern around second inlet 30.

Reactor 10 may be composed of any suitable material which will not react with the reactants used or the organometallic compound to be produced. Suitable materials include, without limitation: glass such as borosilicate glass and PYREX glass; plastics including perfluorinated plastics such as poly(tetrfluoroethylene); quartz; or metal. Metals are preferred, and include, without limitation, nickel alloys and stainless steels. Suitable stainless steels include, but are not limited to, 304, 304 L, 316, 316 L, 321, 347 and 430. Suitable nickel alloys include, but are not limited to, INCONEL, MONEL, and HASTELLOY corrosion-resistant alloys. Optionally, when reactor 10 is composed of a metal, such reactor may be coated with a suitable coating, such as silicon nitride or silicon tetrafluoride, to improve corrosion resistance. Such coatings may be applied by any suitable technique, such as by vapor deposition. The reactor may be composed of a mixture of materials, such as glass-lined stainless steel. The choice of suitable material for the reactor is well within the ability of those skilled in the art. Suitable reactors are generally commercially available from a variety of sources.

The dimensions of reactor 10 are not critical. Reactor 10 may have any suitable length and diameter. The choice of such length and diameter will depend on the volume of the organometallic compound to be produced, and the amount of reaction time needed between the reactants, among other factors within the ability of those skilled in the art. Typical lengths range from 1 to 15 m, preferably from 1.5 to 12 m, more preferably from 1.5 to 10 m, and even more preferably from 1.5 to 8 m. Particularly preferred lengths are 1.5, 2, 3, 4, 5, 6, 7, 8, and 10 m. Typical diameters range from 5 mm to 25 cm, more preferably from 5 mm to 20 cm, still more preferably from 5 mm to 15 cm, yet more preferably from 5 mm to 5 cm, even more preferably from 6 to 25 mm, and most preferably from 8 to 10 mm. Particularly preferred diameters are 5, 6, 7, 8, 9, 10, 12, and 15 mm.

Reactor 10 includes a contacting zone, at least one mixing zone and one or more heat transfer zones. The contacting zone typically extends into the heat transfer zone. Preferably, the contacting zone is contained within a heat transfer zone. More preferably, the contacting zone is co-extensive with a heat transfer zone, or a plurality of heat transfer zones. The length of the contacting zone will depend on the reactants used and the organometallic compound to be produced, whether the reaction is exothermic or endothermic, the efficiency of the mixing section, the velocities of the reactants, and the time needed for the reaction, among other factors within the ability of one skilled in the art. As an example, the contacting zone may comprise from 1 to 99% of the reactor length, preferably from 1 to 95%, more preferably from 1 to 75%, and yet more preferably from 5 to 50%. As the first and second reactant streams in the contacting zone have laminar flow, little mixing occurs in the contacting zone. Instead, reaction between the reactants occurs at the interface of the two streams. In this way, the initial rate of reaction can a controlled.

Figure 6A:
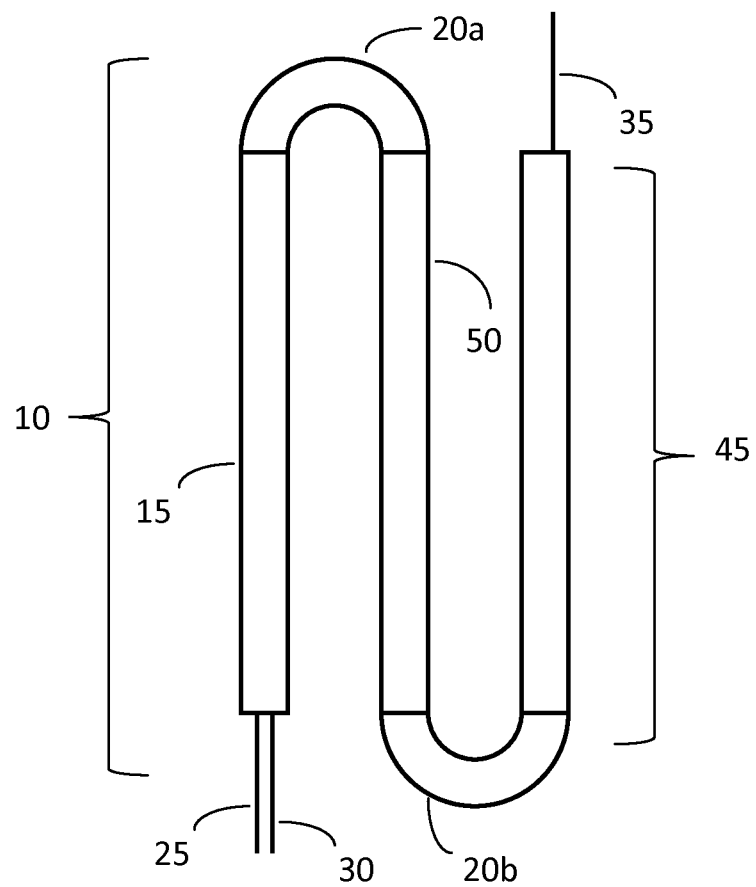
FIGS. 6A-6C are schematic depictions of an apparatus suitable for use with the present invention having a plurality of mixing zones.
Figure 6B:
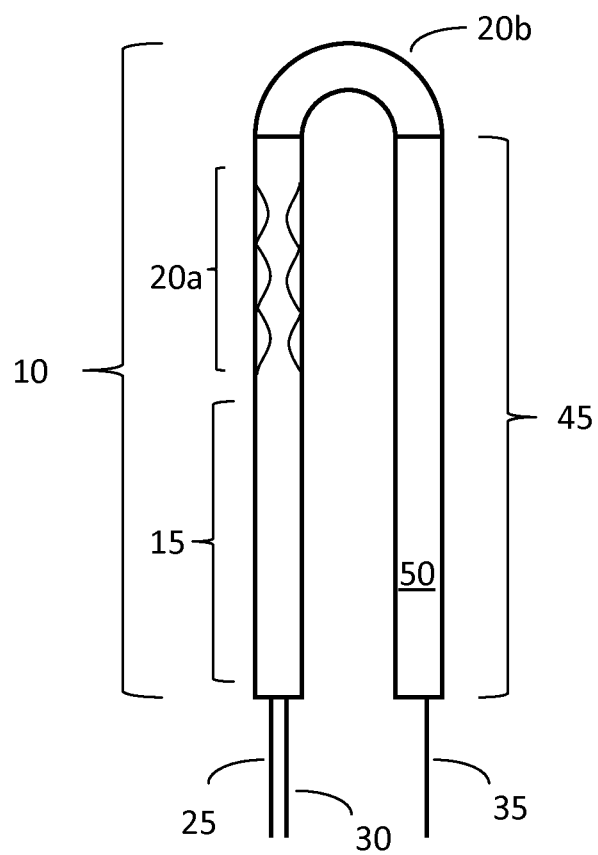
Figure 6C:
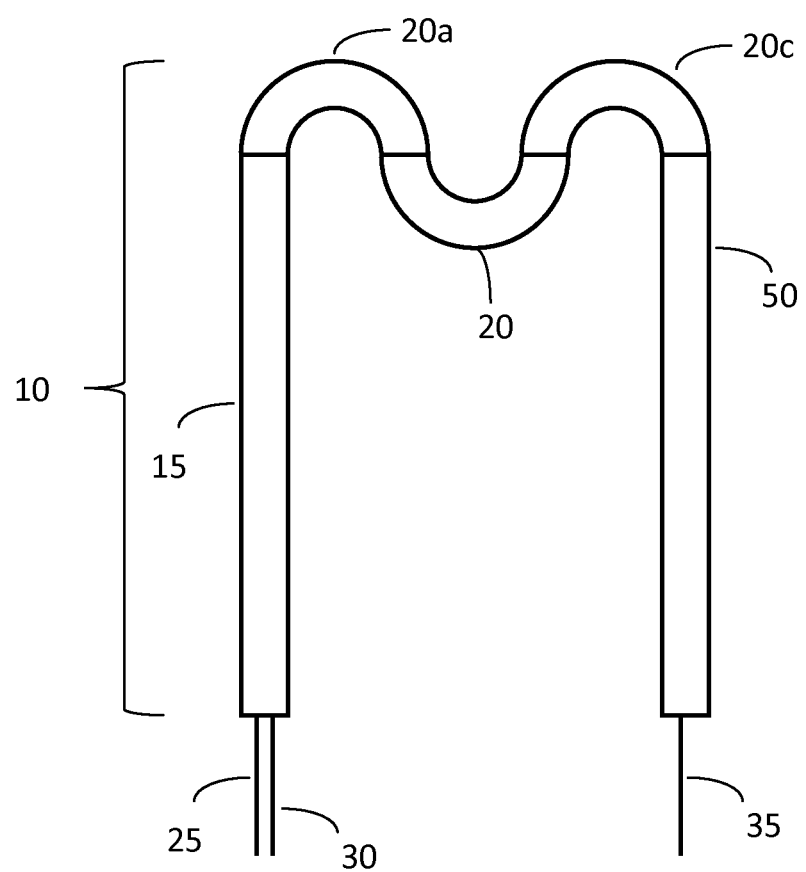

The present reactor contains one or more mixing zones designed to promote turbulence. That is, the mixing zone is designed to promote a flow of the reactant streams that is more turbulent than the laminar flow of the reactants in the contacting zone. The mixing zone may have any suitable design that can be used to control the level of mixing of the reactants. Exemplary mixing zones may include static mixers, venturis, orifices, bends, wavy-walled reactors, and any other suitable mixing means. Preferably, the mixing zone comprises a mixing means chosen from venturis, orifices, bends, wavy-walled reactors and combinations thereof, and more preferably venturis, bends, wavy-walled reactors and combinations thereof. A variety of "bends" may be used as mixing means, such as elbows (having a bend angle of 1-90°), U-bends (having a bend angle of 91-180°), and loops (having a bend angle of 181-360°). Combinations of bends may be employed, such as in a "serpentine" mixing zone, as shown in FIG. 6C. The bends may have any suitable radius of curvature, such as from 0.5 cm to 1 m, preferably from 1 cm to 50 cm, more preferably from 1 cm to 30 cm, and most preferably from 1 to 10 cm. Particularly preferred radii of curvature are 3, 3.2, 3.25, 3.3, 3.5, 3.6, 3.7, 3.8, 4, 4.1, 4.25, 4.5, 4.6, 4.75, 5, 5.1, 5.2, 5.25, 5.5, 5.6, 5.7, 6, 6.1, 6.2, 6.25, 6.3, 6.35, 6.4, 6.5, 7, 7.2, 7.3, 7.4, 7.5, 7.6, 7.7, 76.75, 8, 8.1, 8.25, 8.4, 8.5, 8.6, 8.7, 8.8, 8.9, 9, 9.25, 9.5, 9.75, and 10 cm. The smaller the radius of curvature, the more secondary mixing is promoted.

The choice of the particular mixing means will depend on how exothermic the reaction is. For example, for relatively more exothermic reactions, it is preferred that the mixing zone comprise a mixing means that provides a relatively lesser degree of mixing, such as venturis, bends, wavy-walled reactors, and combinations thereof. It is preferred that the mixing means used for relatively more exothermic reactions provides micro flow regimes rather than complete turbulence. For relatively less exothermic reactions and for endothermic reactions, a mixing zone comprising any suitable mixing means to promote the desired level of mixing may be used. The size of the mixing means may be easily selected by one skilled in the art so as to provide the desired level of mixing.

Such mixing zones may be placed at any suitable point along the reactor. One or more mixing zones may be used in the present reactor. Each mixing zone may include one or more mixing means. When more than one mixing means, such as when more than one mixing zone having a single mixing means or when a single mixing zone having a plurality of mixing means, is used, such mixing means may be the same or different. As used herein, "different mixing means" includes two or more of the same type of mixing means having different sized components, such as two or more venturis having different diameter openings or two or more bends having different radii of curvature. When two or more wavy-walled reactors are used, each such reactor may have different lengths and different radii of the elements composing the wavy-walled section. Preferably, a plurality of mixing means are used. When the present reactor is used to continuously manufacture an organometallic compound through a relatively more exothermic reaction, it is preferred that a plurality of mixing zones are used. It is further preferred that such plurality of mixing zones be composed of different mixing means.

Figure 5A:
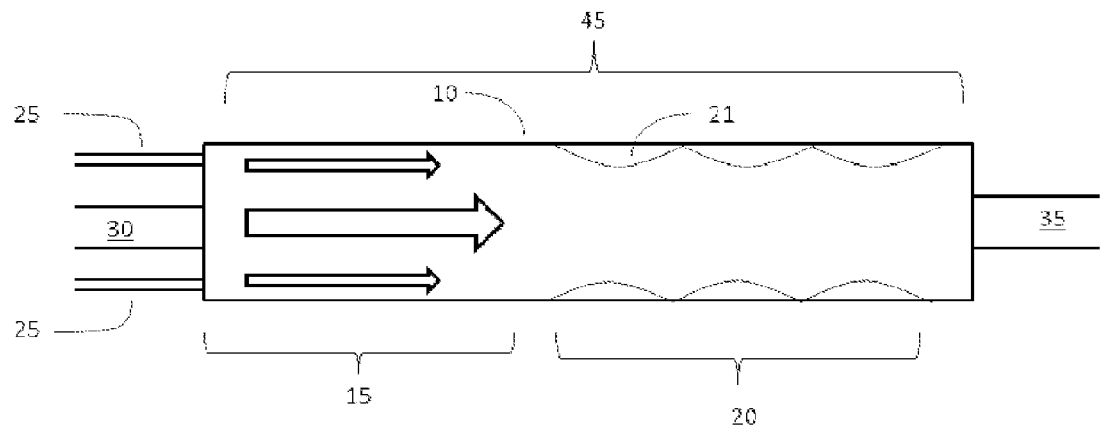
FIGS. 5A-5C are cross-sectional schematic depictions of an apparatus suitable for use with the process of the invention.
Figure 5B:
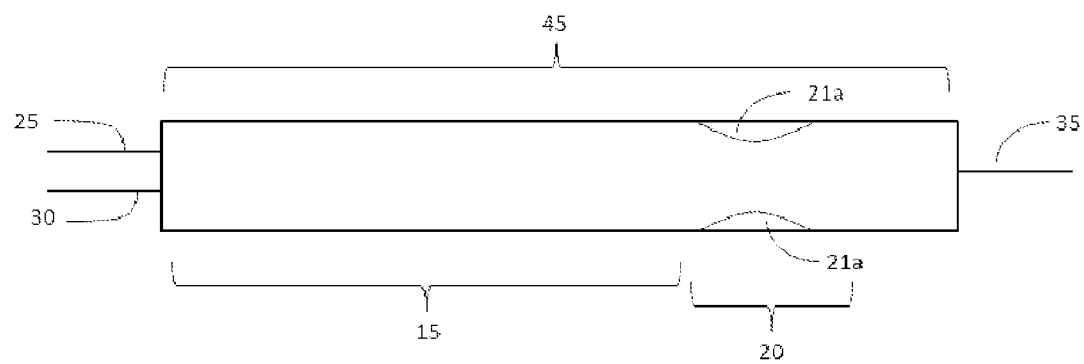
Figure 5C:
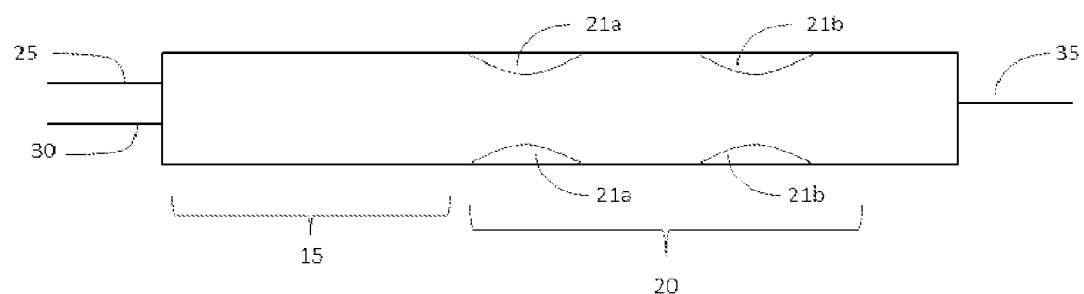

FIG. 3, discussed above, illustrates a U-bend as mixing zone 20. FIG. 5A illustrates a cross-sectional view of reactor 10 having contacting zone 15, mixing zone 20, and heat transfer zone 45 containing both contacting zone 15 and mixing zone 20, where mixing zone 20 is composed of a wavy-walled reactor having elements 21. FIG. 5B illustrates a cross-sectional view of reactor 10 having mixing zone 20 composed of a venture having elements 21*a*. In FIG. 5B, both contacting zone 15 and mixing zone 20 are contained within heat transfer zone 45. FIG. 5C shows a cross-sectional view of reactor 10 having mixing zone 20 composed of a plurality of venturis, 21*a* and 21*b*. A plurality of mixing zones, 20*a* and 20*b*, separated by reaction zone 50 is shown in FIG. 6A, where each mixing zone is a U-bend and each U-bend has a different radius of curvature, not shown. FIG. 6B illustrates a reactor 10 having a plurality of mixing zones, 20*a* and 20*b*, and reaction zone 50 disposed within heat transfer zone 45. Both contacting zone 15 and mixing zone 20*a* are contained within a heat transfer zone, not shown. FIG. 6C illustrates reactor 10 having contacting zone 15, a plurality of mixing zones 20*a*, 20*b*, and 20*c*, and reaction zone 50. In FIG. 6C, the plurality of mixing zones are shown connected in series (a "serpentine" mixing zone), with each of 20*a*, 20*b*, and 20*c* having a different radius of curvature (not shown). Heat transfer zones are not shown in FIGS. 5C, 6A and 6C.

The present reaction may optionally contain a reaction zone following a mixing zone. Preferably, the present reactor does contain at least one reaction zone. When a plurality of mixing zones are used, a reaction zone may be present after any of the mixing zones, and preferably after each mixing zone. The length of the reaction zone will depend on the reactants used and the organometallic compound to be produced, whether the reaction is exothermic or endothermic, the efficiency of the mixing section, the rate of the reaction, and the time needed for the reaction, among other factors within the ability of one skilled in the art. As an example, the reaction zone may comprise from 1 to 99% of the reactor length, preferably from 1 to 95%, more preferably from 1 to 75%, and yet more preferably from 5 to 50%. The contacting zone and any reaction zone may be have the same length or different lengths.

The present reactor also has at least one heat transfer zone. Such heat transfer zone may include any or all of the contacting zone, the mixing zone and the optional reaction zone. Preferably, the heat transfer zone includes the contacting zone and any reaction zone. For example, when a reactor includes both a contacting zone and a reaction zone, each of such zones may be contained within a single heat transfer zone or each may be contained in a separate heat transfer zone. The contacting zone may be composed of one or more heat transfer zones, and preferably one heat transfer zone. Preferably, the contacting zone is co-extensive with a heat transfer zone. It is also preferred that any reaction zone be contained within a heat transfer zone, and more preferably that each reaction zone be co-extensive with a heat transfer zone.

Suitable heat transfer zones include heat exchanges such as condensers, chillers, and heaters. The selection of a specific heat transfer zone, its length and its location in the reactor, will depend on the size of the reactor, the volume of organometallic compound to be produced, whether the reaction to produce the organometallic compound is exothermic or endothermic, and the particular organometallic compound to be produced, among other factors known to those skilled in the art. Such selection of the heat transfer zone and its location in the reactor is within the ability of one skilled in the art.

The first reactant stream enters the contacting zone of the reactor through the first inlet. The first reactant may be in the liquid-phase, the vapor phase or in both liquid- and vapor-phases. Preferably, a majority of the first reactant is in the liquid-phase. The second reactant stream enters the contacting zone of the reactor through the second inlet. The second reactant may be in the liquid-phase, the vapor phase or in both liquid- and vapor-phases. Preferably, a majority of the second reactant is in the liquid-phase. It is also preferred that the first reactant and the second reactant are both in the liquid-phase, the vapor-phase, or in both liquid- and vapor-phases. It is further preferred that both first reactant and second reactant are in the liquid-phase.

Relatively low-melting point solid reactants may be used in the present process by appropriately heating the reactor to a temperature above the melting point of the reactant. Reactants that are either solid or liquid at the temperature of the reactor may be dissolved in a solvent to provide a liquid-phase reactant that is then conveyed into the reactor. An organic solvent is preferred when a reactant or the organometallic compound produced is a solid at the temperature of the reactor. Any organic solvent may be used provided that it does not react with or destabilize the reactants or the organometallic compound produced. Suitable solvents are known to those skilled in the art. Preferred solvents are hydrocarbons such as linear alkyl benzenes, toluene, xylene, mesitylene, durene, quinoline, isoquinoline, squalane, indane, 1,2,3,4-tetrahydronaphthalene (tetralin), and decahydronaphthalene; and ionic liquids. Ionic liquids are generally salts that are liquid at low temperatures, having melting points under 100° C. Ionic liquids are composed entirely of ions and typically they are composed of bulky organic cations and inorganic anions. Due to the high Coulumbic forces in these compounds, ionic liquids have practically no vapor pressure. Any suitable ionic liquid may be employed as the solvent in the present invention. Exemplary cations used in ionic liquids include, but are not limited to, hydrocarbylammonium cation, hydrocarbylphosphonium cation, hydrocarbylpyridinium cation, and dihydrocarbylimidazolium cation. Exemplary anions useful in the present ionic liquids include, without limitation: chlorometalate anion; fluoroborate anion such as tetrafluoroborate anion and hydrocarbyl substituted fluoroborate anion; and fluorophosphate anion such as hexafluorophosphate anion and hydrocarbyl substituted fluorophosphate anion. Exemplary chlorometalate anions include: chloroaluminate anion such as tetrachloroaluminate anion and chlorotrialkylaluminate anion; chlorogallate anions such as chlorotrimethylgallate; and tetrachlorogallate, chloroindate anions such as tetrachloroindate and chlorotrimethylindate.

Dissolving a solid reactant in an organic solvent to provide a liquid-phase reactant allows such solid reactant to be used in the present process. In addition, using an organic solvent allows for the preparation of organometallic compounds according to the present process that might be solid under the conditions of the reactor, and reduces precipitation in the reactor. For example, trimethyl indium, which can be prepared according to the present process, melts at 88° C. and decomposes explosively at 101-103° C. Using an organic solvent in the preparation of trimethyl indium allows for reactor temperatures below its melting point. In addition, trimethyl indium is known to be stable in solution, such as in squalane, at temperatures >125° C. for prolonged periods. Using a solvent such as squalane when preparing trimethyl indium allows for a greater range of reactor temperatures to be employed without decomposing the trimethyl indium.

Any metal-containing compound that can be reacted with a second reactant in a fluid can be used as the first reactant. As used herein, the term "metal" includes "metalloids." The term "metalloid" as used herein refers to boron (Group 13), germanium (Group 14), phosphorus (Group 15), antimony (Group 15) and arsenic (Group 15). Suitable metal-containing first reactants contain at least one metal atom chosen from Group 2-Group 15, preferably from Group 3 to Group 15, and more preferably from Group 4 to Group 15. As used herein, Group 14 metals do not include carbon and silicon and Group 15 metals do not include nitrogen. Particularly preferred metals are those in Groups 3, 4, 5, 8, 9, 10, 11, 12, 13 and 15, even more preferably Groups 4, 5, 8, 11, 12, 13 and 15, and yet more preferably Groups 5, 12, 13 and 15. Exemplary metal atoms include, without limitation, magnesium, calcium, strontium, scandium, yttrium, lutetium, lawrencium, lanthanum, titanium, zirconium, hafnium, cerium, vanadium, niobium, tantalum, chromium, molybdenum, tungsten, manganese, ruthenium, cobalt, rhodium, iridium, nickel, platinum, palladium, copper, silver, gold, zinc, cadmium, aluminum, gallium, indium, silicon, germanium, tin, phosphorus, antimony and antimony. Preferred metal atoms include magnesium, strontium, scandium, yttrium, lutetium, lawrencium, titanium, zirconium, hafnium, vanadium, niobium, tantalum, molybdenum, tungsten, manganese, ruthenium, cobalt, iridium, nickel, platinum, palladium, copper, silver, gold, zinc, cadmium, aluminum, gallium, indium, germanium, antimony and arsenic. It is more preferred that the metal atom is magnesium, scandium, yttrium, lutetium, lawrencium, titanium, zirconium, hafnium, niobium, tantalum, molybdenum, tungsten, ruthenium, cobalt, iridium, nickel, platinum, palladium, copper, silver, gold, zinc, cadmium, aluminum, gallium, indium, germanium, antimony and arsenic, and even more preferred are magnesium, zirconium, hafnium, niobium, tantalum, molybdenum, tungsten, ruthenium, cobalt, iridium, nickel, copper, zinc, cadmium, aluminum, gallium, indium, germanium, antimony and arsenic, and yet more preferred are magnesium, zirconium, hafnium, zinc, cadmium, aluminum, gallium, indium, germanium, antimony and arsenic. Particularly preferred metals are zirconium, hafnium, zinc, cadmium, aluminum, gallium, indium, antimony and arsenic.

Preferred metal-containing compounds useful as the first reactant are the halide, $(C_1-C_4)$carboxylate, amino and hydrocarbyl-containing compounds of a metal atom chosen from Group 2-Group 15. Such preferred metal-containing compounds have the general formula (I)

$$R_a Y_b M^m L \qquad \text{Formula (I)}$$

wherein each R is independently chosen from =H or a ($C_1$-$C_{10}$)hydrocarbyl group; each Y is independently chosen from halide, ($C_1$-$C_4$)carboxylate, ($C_1$-$C_5$)alkoxy, $R^1R^2N$ or a diamino- or tri-amino group; M=Group 2-Group 15 metal; $R^1$ and $R^2$ are independently chosen from H or ($C_1$-$C_6$)alkyl; L=a neutral ligand; m=the valence of M; a=0 to m; b=0 to m; and a+b=m. It will by those skilled in the art that a and b cannot both=0. The term "hydrocarbyl" refers to any hydrocarbon group, and includes alkyl groups and aryl groups. Such hydrocarbyl group may optionally contain atoms other than carbon and hydrogen, such as oxygen or nitrogen. Preferred hydrocarbyl groups are methyl, ethyl, n-propyl, iso-propyl, n-butyl, sec-butyl, iso-butyl, tert-butyl, n-pentyl, neo-pentyl, cyclopentyl, hexyl, cyclohexyl, cyclopentadienyl, methylcyclopentadienyl, pentamethylcyclopentadienyl, ($C_1$-$C_3$)alkoxy($C_2$-$C_6$)alkyl, amidinato, formamidinato, and β-diketonato. When the first reactant contains a hydrocarbyl group, such group is attached to the metal by way of a metal-carbon bond. Exemplary diamino- and tri-amino-groups for Y include, without limitation, 1,2-diaminoethyl, 1,2-di-(N-methylamino)ethyl, 1,3-diaminopropyl, 1,3-di-(N-methylamino)propyl, 1,2-diaminopropyl, and diethylenetriamine Y is preferably chlorine, bromine, acetoxy, methoxy, ethyoxy, propoxy, butoxy, pentoxy, amino, methylamino, dimethylamino, ethylmethylamino, diethylamino, 1,2-diaminoethyl, 1,2-di-(N-methylamino)ethyl, 1,3-diaminopropyl, and 1,3-di-(N-methylamino)propyl. It is more preferred that Y is chlorine, bromine, acetoxy, methoxy, ethyoxy, propoxy, butoxy, pentoxy, amino, methylamino, dimethylamino, ethylmethylamino, and diethylamino.

Neutral ligands (L) may be optional in the metal-containing reactants. Such neutral ligands do not bear an overall charge and may function as stabilizers. Neutral ligands include, without limitation, CO, NO, nitrogen ($N_2$), amines, phosphines, alkylnitriles, alkenes, alkynes, and aromatic compounds. The term "alkene" includes any aliphatic compound having one or more carbon-carbon double bonds. Exemplary neutral ligands include, but are not limited to: ($C_2$-$C_{10}$)alkenes such as ethene, propene, 1-butene, 2-butene, 1-pentene, 2-pentene, 1-hexene, 2-hexene, norbornene, vinylamine, allylamine, vinyltri($C_1$-$C_6$)alkylsilane, divinyldi($C_1$-$C_6$)alkylsilane, vinyltri($C_1$-$C_6$)alkoxysilane and divinyldi($C_1$-$C_6$)alkoxysilane; ($C_4$-$C_{12}$)dienes such as butadiene, cyclopentadiene, isoprene, hexadiene, octadiene, cyclooctadiene, norbornadiene and α-terpinene; ($C_6$-$C_{16}$)trienes; ($C_2$-$C_{10}$)alkynes such as acetylene and propyne; and aromatic compounds such as benzene, o-xylene, m-xylene, p-xylene, toluene, o-cymene, m-cymene, p-cymene, pyridine, furan and thiophene. The number of neutral ligands depends upon the particular metal chosen for M. When two or more neutral ligands are present, such ligands may be the same or different.

It is further preferred that the first reactant has the formula (II) $R^3_cY^1_dM^2L_n$, wherein each $R^3$ is chosen from H or ($C_1$-$C_4$)alkyl; each $Y^1$ is chosen from halide; $M^2$ is a Group 13 metal; L is as defined above; c=0-3; d=0-3; c+d=3; and n=0-1. $R^3$ is preferably H, methyl or ethyl. $Y^1$ is preferably chlorine or bromine. In formula II, when L is present, it is preferred that the neutral ligand is a tertiary amine or tertiary phosphine. It is preferred that $M^2$ is indium or gallium. Preferred tertiary amines and tertiary phosphines are tri($C_1$-$C_4$)alkylamines and tri($C_1$-$C_4$)alkylphosphines.

Suitable second reactants may be any of the above described metal-containing compounds useful as the first reactant. Other compounds useful as the second reactant include, without limitation, compounds suitable for alkylating the first reactant or acting as a ligand for the metal atom in the first reactant. In addition to the metal-containing compounds of formula I, other preferred compounds useful as the second reactant are: alkylamines; alkylphosphines; alkali metal or alkaline earth metal salts of β-diketonates, amidinates, formamidinates, guanidinates, and cyclopentadienyls; ($C_1$-$C_4$)alkoxides; ($C_1$-$C_6$)alkyl lithium compounds; and ($C_1$-$C_6$)alkyl Grignard reagents. Suitable alkylamines are mono-, di-, and tri-($C_1$-$C_6$)alkylamines, preferably mono-, di-, and tri-($C_1$-$C_4$)alkylamines, and more preferably tri-($C_1$-$C_4$)alkylamines. Particularly preferred alkylamines are trimethylamine, triethylamine, and tripropylamine. Suitable alkylphosphines are mono-, di-, and tri-($C_1$-$C_6$)alkylphosphines, preferably mono-, di-, and tri-($C_1$-$C_4$)alkylphosphines, and more preferably tri-($C_1$-$C_4$)alkylphosphines. Particularly preferred alkylphosphines are trimethylphosphine, triethylphosphine, and tripropylphosphine. The salts of β-diketonates, amidinates, formamidinates, guanidinates, and cyclopentadienyls are easily prepared by reacting the corresponding β-diketone, amidinine, formamidine, guanidine or cyclopentadiene with a suitable base, such as sodium hydride. It is preferred that such salts are alkali metal salts. Suitable amidines and formamidines are those disclosed in U.S. Pat. No. 2006/0141155 and U.S. Pat. No. 2008/0305260. Preferred cyclopentadienes are cyclopentadiene, methylcyclopentadiene and pentamethylcyclopentadiene. It will be appreciated by those skilled in the art that the first reactant and the second reactant are different.

It is preferred that the second reactant is chosen from alkylamines, alkylphosphines and compounds of formula (II) described above. It is further preferred that the second reactant is chosen from tri($C_1$-$C_4$)alkylamines, tri($C_1$-$C_4$)alkylphosphines and compounds of formula (II) described above, wherein $M^2$ is chosen from indium and gallium, and wherein $Y^1$ is chosen from chlorine and bromine.

The first reactant and the second reactant, either of these reactants optionally being in an organic solvent, are conveyed into the contacting zone of the reactor unit and subjected to conditions which provide controlled mixing of the reactants in the one or more mixing zones. Controlling mixing of the reactants allows for more precise control of the overall reaction leading to the organometallic compound. Mixing is controlled in the present process by controlling the flows of the reactants in the laminar regime in the contacting zone and by the degree of mixing in the mixing zone. The reactants are introduced into the contacting zone of the reactor in a manner so as to have cocurrent and substantially laminar flow. By "substantially laminar," it is meant that the flow of each reactant stream entering the mixing zone has a Reynolds number ("Re") of ≤2100, preferably ≤2000, more preferably ≤1500, and most preferably ≤1000. It is further preferred that the flows of the first reactant stream and the second reactant stream are concentric. When the reactant streams have concentric flows, it is preferred that the center reactant stream has a lower Re than the outer reactant stream. The first reactant and second reactant can react at the interface of the reactant streams in the contacting zone. This provides for a very controlled rate of reaction to for the organometallic compound, particularly for exothermic reactions. The reactant streams then enter the mixing zone where a greater degree of mixing is achieved, with a consequent increase in the rate of reaction, particularly for exothermic reactions. Control of the degree of mixing of the reactants allows for the production of organometallic compounds in higher overall yields with reduced amounts of reaction by-products.

Once the first and second reactants are mixed, the resulting reaction mixture stream is subjected to conditions sufficient to allow the reactants to react to form the desired organometallic compound. Such conditions are well known to those skilled in the art, and may include heating, cooling, or a combination thereof. For exothermic reactions, the heat transfer zone of the reactor unit will contain a cooling unit in order to control the rate of reaction. For endothermic reactions, the heat transfer zone will contain a heating unit. Reaction time is controlled by controlling the residence time of the reactants in the reactor unit.

Following the reaction, the reaction mixture stream, which now includes the organometallic compound produced, any unreacted first and second reactants, reaction byproducts, and any organic solvent used, exits the reactor unit through the outlet in the heat transfer zone. Typically, the organometallic compound is obtained in a yield of ≥70% prior to any purification steps. Preferably, the organometallic compound is obtained in ≥90% yield, more preferably ≥95%, still more preferably ≥97%, and even more preferably ≥98%.

The organometallic compound produced, unreacted first and second reactants, reaction byproducts, and any organic solvent are conveyed from the outlet of the reactor unit to a separation unit. Such separation unit may employ any conventional technique for purification of the organometallic compound, including, for example, crystallization, distillation or sublimation. Such separation techniques are well-known in the art. Preferably, the organometallic compound is obtained in a purity of ≥95%, more preferably ≥97%, still more preferably ≥98%, yet more preferably ≥99%, even more preferably ≥99.99%, and most preferably ≥99.9999%.

The present continuous process is suitable to prepare a wide range of organometallic compounds. Preferred organometallic compounds are those of the formula $R^4_e M^m X_{m-e} L^1$ (formula III), where each $R^4$ is independently $(C_1-C_{20})$alkyl, $(C_2-C_{20})$alkenyl, $(C_2-C_{20})$alkynyl, $(C_5-C_{20})$aryl, $(C_5-C_{20})$aryl$(C_1-C_{10})$alkyl, $(C_1-C_{20})$alkoxy, $(C_2-C_{10})$carbalkoxy, amino, $(C_1-C_{12})$alkylamino$(C_1-C_{12})$alkyl, di$(C_1-C_{20})$alkylamino$(C_1-C_{12})$alkyl, phosphino, and a divalent ligand; each X is independently H, $R^4$, cyano, and halogen; $L^1$=a neutral ligand; e=the valence of the $R^4$ group and is an integer ≥1; and m=the valence of M. The "amino" groups include —$NH_2$, $(C_1-C_{12})$alkylamino, and di$(C_1-C_{12})$alkylamino. Preferably, the amino groups are —$NH_2$, $(C_1-C_6)$alkylamino, and di$(C_1-C_6)$alkylamino, and more preferably —$NH_2$, $(C_1-C_4)$alkylamino, and di$(C_1-C_4)$alkylamino. "Phosphino" groups include —$PH_2$, $(C_1-C_{12})$alkylphosphino, and di$(C_1-C_{12})$alkylphosphino, preferably include —$PH_2$, $(C_1-C_6)$alkylphosphino, and di$(C_1-C_6)$alkylphosphino, and more preferably include —$PH_2$, $(C_1-C_4)$alkylphosphino, and di$(C_1-C_4)$alkylphosphino. The above $R^4$ groups may optionally be substituted by replacing one or more hydrogen atoms with one or more substituent groups, such as halogen, carbonyl, hydroxyl, cyano, amino, alkylamino, dialkylamino, and alkoxy. For example, when $R^4$ is a $(C_1-C_{20})$alkyl group, such group may contain a carbonyl within the alkyl chain. Suitable divalent ligands include, without limitation, β-diketonates, amidinates, formamidinates, phosphoamidinates, guanidinates, β-diketiminates, bicyclic amidinates and bicyclic guanidinates. Preferred divalent ligands include β-diketonates, amidinates, formamidinates, phosphoamidinates, and guanidinates. Depending on the particular metal atom, the organometallic compounds of formula III may optionally contain one or more neutral ligands (L). Such neutral ligands do not bear an overall charge. Neutral ligands include, without limitation, CO, NO, nitrogen, amines, ethers, phosphines, alkylphosphines, arylphosphines, nitriles, alkenes, dienes, trienes, alkynes, and aromatic compounds. Adducts of organometallic compounds of formula III with amines or phosphines, such as tertiary amines or tertiary phosphines, are contemplated by the present invention.

Preferably, each $R^4$ group in formula III is independently selected from $(C_1-C_{10})$alkyl, $(C_2-C_{10})$alkenyl, $(C_2-C_{10})$alkynyl, $(C_5-C_{15})$aryl, $(C_5-C_{10})$aryl$(C_1-C_6)$alkyl, $(C_1-C_{10})$alkoxy, $(C_2-C_{10})$carbalkoxy, amino, $(C_1-C_6)$alkylamino$(C_1-C_6)$alkyl, di$(C_1-C_6)$alkylamino$(C_1-C_6)$alkyl, phosphino, and a divalent ligand; and more preferably $(C_1-C_6)$alkyl, $(C_2-C_6)$alkenyl, $(C_2-C_6)$alkynyl, $(C_5-C_{10})$aryl, $(C_5-C_8)$aryl$(C_1-C_6)$alkyl, $(C_1-C_6)$alkoxy, $(C_2-C_6)$carbalkoxy, amino, $(C_1-C_4)$alkylamino$(C_1-C_6)$alkyl, di$(C_1-C_4)$alkylamino$(C_1-C_6)$alkyl, phosphino, and a divalent ligand. It is further preferred that each $R^4$ is independently selected from $(C_1-C_5)$alkyl, $(C_2-C_3)$alkenyl, $(C_2-C_3)$alkynyl, $(C_5-C_8)$aryl, $(C_5-C_8)$aryl$(C_1-C_4)$alkyl, $(C_1-C_5)$alkoxy, $(C_2-C_5)$carbalkoxy, amino, $(C_1-C_4)$alkylamino$(C_1-C_4)$alkyl, di$(C_1-C_4)$alkylamino$(C_1-C_4)$alkyl, phosphino, and a divalent ligand, and still more preferably $(C_1-C_4)$alkyl, $(C_2-C_3)$alkenyl, $(C_5-C_8)$aryl, $(C_1-C_5)$alkoxy, amino, $(C_1-C_3)$alkylamino$(C_1-C_4)$alkyl, di$(C_1-C_3)$alkylamino$(C_1-C_4)$alkyl, phosphino, and a divalent ligand.

Preferred organometallic compounds have the structure of formula (IV)

$$R^5_x X^2_{p-x} M^{3p} \qquad \text{Formula (IV)}$$

wherein each $R^5$ is independently chosen from $(C_1-C_6)$alkyl, $(C_2-C_6)$alkenyl, $(C_1-C_4)$alkylamino$(C_1-C_6)$alkyl, di$(C_1-C_4)$alkylamino$(C_1-C_6)$alkyl, $(C_5-C_{10})$aryl, —$NH_2$, $(C_1-C_4)$alkylamino, and di$(C_1-C_4)$alkylamino; each $X^2$ is independently chosen from H, halogen, $(C_1-C_{10})$alkoxy and $R^5$; $M^3$ is a Group 2, 4 or 13 metal; x is the valence of the $R^5$ group and is an integer; p is the valence of $M^3$; and 1≤x≤p. Adducts of organometallic compounds of formula II with amines or phosphines, such as tertiary amines or tertiary phosphines, are contemplated by the present invention. It is preferred that each $R^5$ is independently chosen from $(C_1-C_4)$alkyl, $(C_2-C_4)$alkenyl, $(C_5-C_{10})$aryl, —$NH_2$, $(C_1-C_4)$alkylamino, and di$(C_1-C_4)$alkylamino; and more preferably $(C_1-C_4)$alkyl, $(C_5-C_8)$aryl, —$NH_2$, $(C_1-C_4)$alkylamino, and di$(C_1-C_4)$alkylamino. Exemplary groups for R1 include, without limitation, methyl, ethyl, n-propyl, iso-propyl, butyl, tert-butyl, iso-butyl, sec-butyl, n-pentyl, iso-pentyl, neo-pentyl, vinyl, allyl, propargyl, aminomethyl, aminoethyl, aminopropyl, dimethylaminopropyl, phenyl, cyclopentadienyl, methylcyclopentadienyl, pentamethylcyclopentadienyl, methylamino, dimethylamino, and ethylmethylamino. When $X^2$ is a halogen, chlorine and bromine are preferred and chlorine is more preferred. When $M^3$ is a Group 2 metal, x=1 or 2. When $M^3$ is a Group 4 metal, x=1, 2, 3 or 4. When $M^3$=a Group 13 metal, x=1, 2 or 3. $M^3$ is preferably magnesium, zirconium, hafnium, aluminum, indium or gallium, and more preferably aluminum, indium or gallium.

Exemplary organometallic compounds include, but are not limited to: trialkyl indium compounds such as trimethyl indium, triethyl indium, tri-n-propyl indium, tri-iso-propyl indium, dimethyl iso-propyl indium, dimethyl ethyl indium, dimethyl tert-butyl indium, methyl di-tert-butyl indium, methyl di-isopropyl indium, and tri-tertiarybutyl indium; trialkyl indium-amine adducts; dialkyl haloindium compounds such as dimethyl indium chloride; alkyl dihaloindium compounds such as methyl dichloroindium; cyclopentadienyl indium; trialkyl indium-trialkyl-phosphine adducts such as trimethyl indium-trimethyl phosphine adduct; trialkyl gallium compounds such as trimethyl gallium, triethyl gallium, tri-iso-propyl gallium, tri-tert-butyl gallium, dimethyl iso-propyl gallium, diethyl tert-butyl gallium, methyl di-iso-propyl gallium, dimethyl tert-butyl gallium, dimethyl neo-pentyl gallium, and methyl ethyl iso-propyl gallium; trialkyl gallium-amine adducts; trialkyl gallium-phosphine adducts; alkyl dihalogallium compounds such as methyl dichlorogallium, ethyl dichlorogallium and methyl dibromogallium; dialkyl halogallium compounds such as dimethyl gallium chloride and diethyl gallium chloride; trialkylaluminum compounds such as trimethyl aluminum, triethyl aluminum, tri-n-propyl aluminum, tri-iso-propyl aluminum, tri-tert-butyl aluminum, dimethyl iso-propyl aluminum, dimethyl ethyl aluminum, dimethyl tert-butyl aluminum, methyl di-tert-butyl aluminum, and methyl di-iso-propyl aluminum; diaklyl haloaluminum compounds such as dimethyl aluminum chloride and diethylaluminum chloride; alkyl dihaloaluminum compounds such as methyl aluminum dichloride, ethyl aluminum dichloride, and ethyl aluminum dibromide; metal dialkylamido compounds such as tetrakis(ethylmethylamino) zirconium and tetrakis(ethylmethylamino) hafnium; metal beta-diketonates such as beta-diketonates of hafnium, zirconium, tantalum and titanium; and metal amidinates such as amidinates of copper, lanthanum, ruthenium, and cobalt. For example, Group 13 organometallic compounds may be prepared using the reactants described in, for example, U.S. Pat. Nos. 5,756,786; 6,680,397; and 6,770,769. Metal amidinate compounds may be prepared using the reactants described in, for example, U.S. Pat. Nos. 7,638,645; and 7,816,550.

The organometallic compounds prepared by the present process may be used in a variety of applications that demand the use of high purity organometallic compounds, such as in certain catalyst applications and in the manufacture of electronic devices such as light emitting diodes. The present organometallic compounds may also be used as intermediates in the preparation of other organometallic compounds.

Example 1

The following table illustrates various organometallic compounds to be produced according to the present process. Suitable organic solvents are listed where such solvents are needed or may be optionally used.

| Compound | First Reactant | Second Reactant | Solvent |
|---|---|---|---|
| TDMAHf | $HfCl_4$ | $(CH_3)_2NLi$ | Mesitylene or durene |
| TDMAZr | $ZrCl_4$ | $(CH_3)_2NLi$ | Mesitylene or durene |
| TEMAHf | $HfCl_4$ | $(CH_3)(CH_3CH_2)NLi$ | Mesitylene or durene |
| TEMAZr | $ZrCl_4$ | $(CH_3)(CH_3CH_2)NLi$ | Mesitylene or durene |
| $(CH_3)_2InCl$ | $InCl_3$ | $(CH_3)_3Al$ | Squalane or mesitylene |
| $(CH_3)_3Ga$ | $GaCl_3$ | $(CH_3)_3Al$ | Toluene or mesitylene |
| $(CH_3)_3In$ | $InCl_3$ | $(CH_3)_3Al$ | Squalane or mesitylene |
| $(CH_3CH_2)_3Ga$ | $GaCl_3$ | $(CH_3CH_2)_3Al$ | Toluene or LAB |
| $(CH_3CH_2)_3In$ | $InCl_3$ | $(CH_3CH_2)_3Al$ | Squalane or mesitylene |
| $(CH_3CH_2)_2GaCl$ | $GaCl_3$ | $(CH_3CH_2)_3Al$ | Toluene or LAB |

The abbreviations have the following meanings: LAB=linear alkyl benzenes; TDMA=tetrakis(dimethylamino) or $[(CH_3)_2N]_4$; and TEMA=tetrakis(ethylmethylamino) or $[(CH_3)(CH_3CH_2)N]_4$.

Example 2

To a reactor having a contacting zone having first and second inlets, multiple heat transfer zones, a plurality of mixing zones having different radii of curvature, and a reaction zone following each mixing zone was fed a predominantly liquid stream of TMA at 200-300 kPa as a first reactant at a temperature of 10-30° C. at a flow rate of 10-20 units/hr and a predominantly liquid stream of tripropylamine ("TPA") as a second reactant also at 200-300 kPa and a temperature of 10-30° C. at a flow rate of 20-40 units/hour into a laminar environment of a reactor inlet. The flow rates were set to control a molar excess of TPA at slightly more than 1/1 to TMA. Both reactant streams were delivered to the mixing zone of the reactor having concentric and substantially laminar flows. The Reynolds number for each reactant stream entering the mixing zone was ≤1000. The reactant streams had a total residence time in the reactor of >20 seconds. Upon exiting the reactor, the product (TMA-TPA adduct) stream was conveyed to a separation unit to remove impurities. This reaction was operated mostly continuously for more than 24 hours with only a few short interruptions resulting in a production of >450 kg of material.

Example 3

To a reactor similar to that used in Example 2, was fed a predominantly liquid stream of TMA-TPA adduct from Example 2 as a first reactant at a pressure of 200-300 kPa, a temperature of 40-60° C. and at a flow rate of 20-40 units/hr and a predominantly liquid stream of gallium chloride in a aromatic hydrocarbon solvent as a second reactant at a temperature of 2-10° C. and a pressure of 200-300 kPa and at a flow rate of 20-40 units/hr to maintain a molar ratio of aluminum to gallium metal at greater than 1/1. The heat transfer zone of the reactor maintained the reactor outlet temperature of 85-100° C. The reactor was operated continuously for more than 24 hours and during this time the product (trimethylgallium or "TMG") was continuously purified in a separation unit producing more than 100 kg of high purity TMG at an overall yield of >85%.

Example 4

The procedure of Example 3 was repeated and the overall yield after purification was >90%.

Example 5

The procedure of Example 2 is repeated except that triethylaluminum is used as the first reactant to produce triethylaluminum-TPA adduct.

Example 6

The procedure of Example 3 is repeated except that the triethylaluminum-TPA adduct from Example 5 is used as the first reactant to produced triethylgallium.

Example 7

The procedure of Example 3 is repeated except that lithium dimethylamide in mesitylene is used as the first reactant and hafnium tetrachloride in mesitylene is used as the second reactant to produce tetrakis(dimethylamino) hafnium.

Example 8

The procedure of Example 7 is repeated except that hafnium tetrachloride is replaced with zirconium tetrachloride to produce tetrakis(dimethylamino) hafnium.

Example 9

The procedure of Example 7 is repeated except that lithium ethylmethylamide in mesitylene is used as the first reactant to produce tetrakis(ethylmethylamino) hafnium.

What is claimed is:

1. An apparatus for continuously manufacturing an organometallic compound comprising: (a) a source of a first reactant stream wherein the first reactant comprises a metal; (b) a source of a second reactant stream; (c) a laminar flow contacting zone for cocurrently contacting the first reactant stream and the second reactant stream; (d) a mixing zone comprising a turbulence-promoting device; and (e) a heat transfer zone.

2. The apparatus of claim 1 wherein the turbulence-promoting device is chosen from bends, spirals, venturis, wavy-walled columns, orifices and static mixers.

3. The apparatus of claim 2 wherein the turbulence-promoting device is chosen from venturis, bends, wavy-walled reactors and combinations thereof.

4. The apparatus of claim 1 further comprising a plurality of turbulence-promoting devices.

5. The apparatus of claim 4 wherein the plurality of turbulence-promoting devices comprises at least 2 different mixing zones.

6. The apparatus of 1 further comprising a plurality of mixing zones with turbulence-promoting devices.

7. The apparatus of claim 1 further comprising a reaction zone following the mixing zone.

* * * * *